(12) United States Patent
Kobayashi et al.

(10) Patent No.: US 6,375,671 B1
(45) Date of Patent: Apr. 23, 2002

(54) CLOSURE DEVICE FOR TRANSCATHETER OPERATIONS

(75) Inventors: Toshiki Kobayashi, Kawagoe; Yoshikazu Kishigami; Katsuya Miyagawa, both of Osaka, all of (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/551,606

(22) Filed: Apr. 17, 2000

(30) Foreign Application Priority Data

Apr. 19, 1999 (JP) .......................................... 11-111171

(51) Int. Cl.[7] .............................................. A61B 17/08
(52) U.S. Cl. .......................................... 606/213; 606/151
(58) Field of Search ........................... 604/93.01, 104, 604/105, 106, 264, 530, 531, 532, 533, 507; 606/1, 151, 213, 215

(56) References Cited

U.S. PATENT DOCUMENTS 5,861,003 A    1/1999   Latson et al.
6,063,113 A  * 5/2000   Kavteladze et al.
6,063,133 A  * 5/2000   Kavteladze et al.

FOREIGN PATENT DOCUMENTS

| GB | WO-99/07292 | * | 5/1998 |
| JP | A7308331 | | 11/1995 |
| WO | WO2641692 A | | 7/1990 |
| WO | WO9802100 A | | 1/1998 |
| WO | WO9827868 A | | 7/1998 |
| WO | WO-98/27868 | * | 7/1998 |
| WO | WO9907292 A | | 2/1999 |

* cited by examiner

Primary Examiner—Glenn K. Dawson
Assistant Examiner—Catherine Serke

(57) ABSTRACT

A closure device for transcatheter operations includes a longitudinally elasticated fixing member (1) having a shape-restoring force and being provided with a relatively large-sized, first and second circular portion (11,12) at both ends thereof, and a closure membrane (2) attached to the first circular portion (11) and closing up a ring thereof. The first circular portion (11) is fixed by a connecting portion extending from the fixed circular portion and progressively decreasing in size toward the second circular portion. The second circular portion may be provided with a holding portion (13) as occasion demands.

6 Claims, 8 Drawing Sheets

CLOSURE DEVICE FOR TRANSCATHETER OPERATIONS

BACKGROUND OF THE INVENTION

1. Field of the Invention

The present invention relates to a closure device suitable for transcatheter operations, i.e., operations for closing and repairing intracardiac or vascular defects.

2. Description of Background Art

In general, shunt affections due to congenital cardiac anomalies have been treated by surgical operations. Such surgical treatments consequently require not only the treatment of the affected area but also thoracotomy that imposes a burden on the patient. In particular, the surgical treatment is a great burden to a child patient. For this reason, there has recently been developed a noninvasive procedure in which the intracardiac defect is repaired with a cardiac catheter adapted to be inserted transvascularly into a cardiac cavity.

For example, patent ductus arteriosus (PDA) that is one of shunt affections, has been treated so far by transvascularly inserting a closure device into a blood vessel with a catheter and then leaving it in the blood vessel to obstruct the blood flow passing therethrough. In this method, the patent ductus arteriosus is closed by introducing a spongy polyvinyl alcohol closure device, which is previously formed into a shape corresponding to the size and morphology of the arterial duct, into the diseased site to be treated through the femoral artery. Porstman reported the first clinical success of this method in 1967. On the other hand, Rashkind proposed a method of closing a patent ductus arteriosus with a closure device composed of united double umbrella-like members and adapted to be introduced into the diseased site through a femoral vein by a catheter.

However, the Porstman's method is complex in operation and includes a high risk of injuring vessels since it is required to insert a closure device with a larger size than the arterial duct through the femoral artery, thus making it difficult to apply it to infant patients. On the other hand, the Rashkind's method involves a problem such that the residual shunts appear frequently.

As a solution of the above problem, Japanese Patent unexamined publication No. 07-308331 discloses a tool for obstructing intracorporeal tubular cavity that consists of a shape-memory alloy provided with a ring at both ends and is recoverable into a conical coil shape toward the central part of the coil at a predetermined temperature around the body temperature. This tool is adapted to obstruct a shunt site by introducing it into the shunt site and allowing a thrombus to adhere to the coil portion, and thus it has a problem such that a leakage takes place frequently.

On the other hand, as a clinical closure device, straight coils have been put to practical use currently. However, the straight coil has the problem that the leakage occurs frequently as is the case with the shape-memory alloy coil. In addition, it has a trouble in fixing it on a morbid part and tends to cause total dislocation or dislodgement.

SUMMARY OF THE INVENTION

The present invention has been developed in view of the above circumstances and aims at providing a closure device for transcatheter operations, which is applicable to defects with any form at a low risk of injury of blood vessels and free from leakage and residual shunts.

The present inventors dedicated efforts to solution of the above problems and achieved the present invention on the basis of an idea of combining an easily-foldable flat closure member with a shape-restoring force and a longitudinally elasticated fixing member with a shape-restoring force.

According to the present invention, there is provided a closure device for transcatheter operations, comprising:

a longitudinally elasticated fixing member having a shape-restoring force, the fixing member having a relatively large-sized circular portion at both ends thereof, at least one of the circular portions being fixed in a ring and connected to the opposite circular portion by means of a connecting portion, said connecting portion being extended from the fixed circular portion and progressively decreased in size toward the opposite circular portion; and a closure membrane attached to said fixed circular portion for closing a defect.

In this case, the opposite or second circular portion may be fixed in a ring as well as the first circular portion. When the second circular portion is not fixed in a ring and thus has a free end, the second circular portion is provided at the free end thereof with a holding portion. The holding portion is generally formed into a small-sized ring. Further, the second circular portion is generally formed so as to have the same diameter as the first circular portion. If the second circular portion is fixed in a ring, the ring may be closed up with a closure membrane as well as the first circular portion.

As a closure membrane for closing the ring, it is preferred to use a fabric or non-woven fabric of a biocompatible material. The fixing member is preferably made of a wire of a superelastic metal or a shape-memory alloy with a transformation temperature ranging from 30 to 36° C. and formed into a coil or zigzag.

Further scope of applicability of the present invention will become apparent form the detailed description given hereinafter. However, it should be understood that the detailed description and specific example, while indicating preferred embodiments of the invention, are given by way of illustration only; since various changes and modifications within the spirit an scope of the invention will become apparent to those skilled in the art form the detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
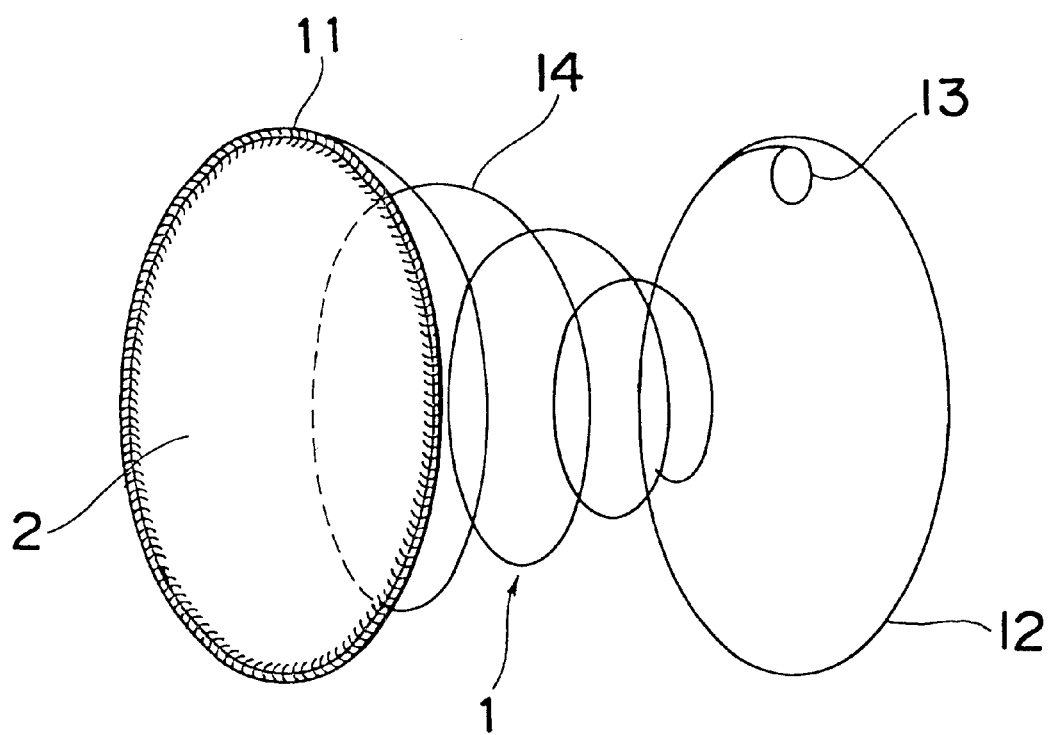
FIG. 1 is a perspective view illustrating one embodiment of a closure device for transcatheter operations according to the present invention.
Figure 3:
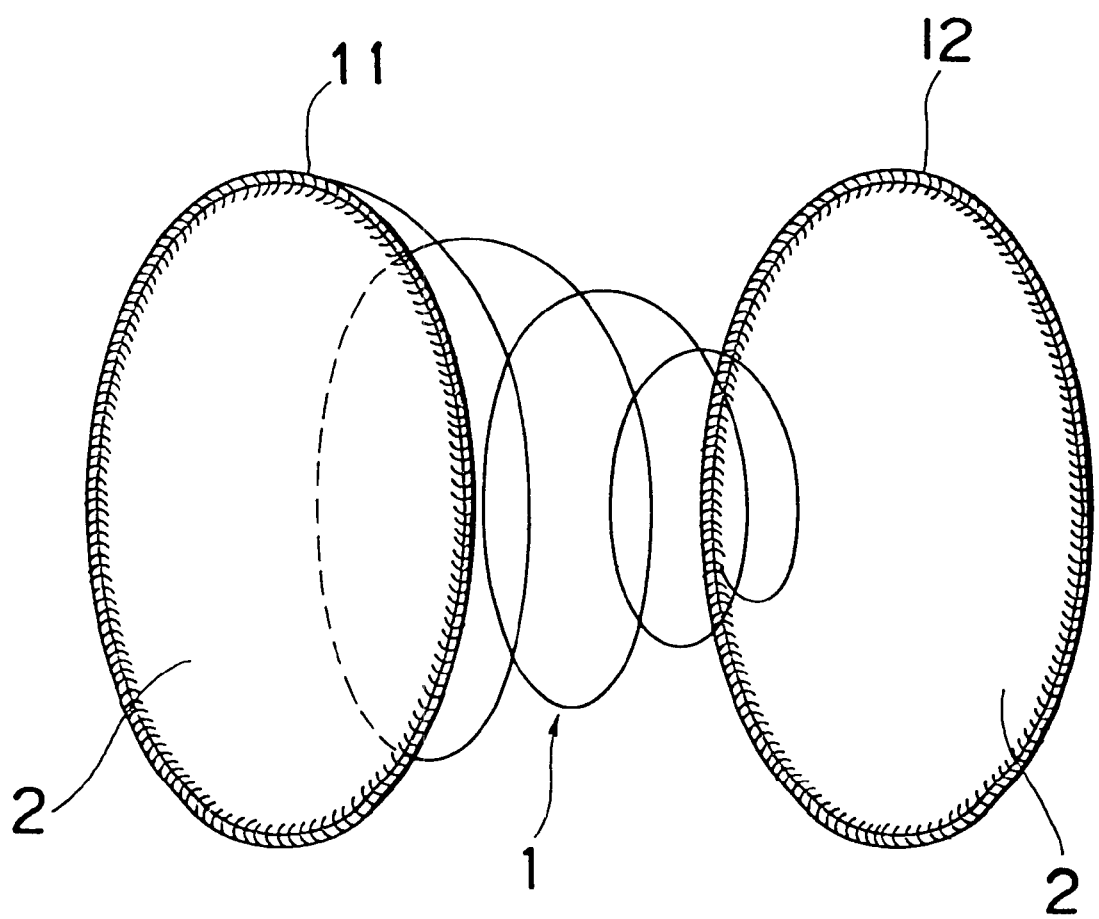
FIG. 3 is a perspective view illustrating still another embodiment of a closure device for transcatheter operations according to the present invention.

Referring now to FIGS. 1 and 3, there are shown closure devices for transcatheter operations according to the present invention. The closure device comprises a fixing member 1 having a relatively large-sized, first and second circular portion 11, 12 at both ends thereof, and a closure membrane 2 attached thereto for closing a ring of the first circular portion 11 of the fixing member 1. The first circular portion 11 is fixed in a ring, connected to the second circular portion 12 by a longitudinally elasticated connecting portion 14. The connecting portion 14 extends from the first circular potion, progressively decreases in size toward the second circular portion 12 and is joined to thereto.

The fixing member 1 is a longitudinally elasticated member having a shape-restoring force and has first and second circular portions 11 and 12 of a relatively large-sized diameter at both ends thereof. At least one of the circular portions (first circular portion 11 in the drawings) is fixed in a relatively large-sized ring by welding or any other suitable joint means. The ring of the first circular portion 11 is closed up or covered with the closure membrane 2. The longitudinally elasticated connecting portion 14 extending from the fixed circular portion 12 is spiraled, progressively decreases in diameter toward the opposite or second circular portion 12 and is connected to the second circular portion 12.

Figure 4:
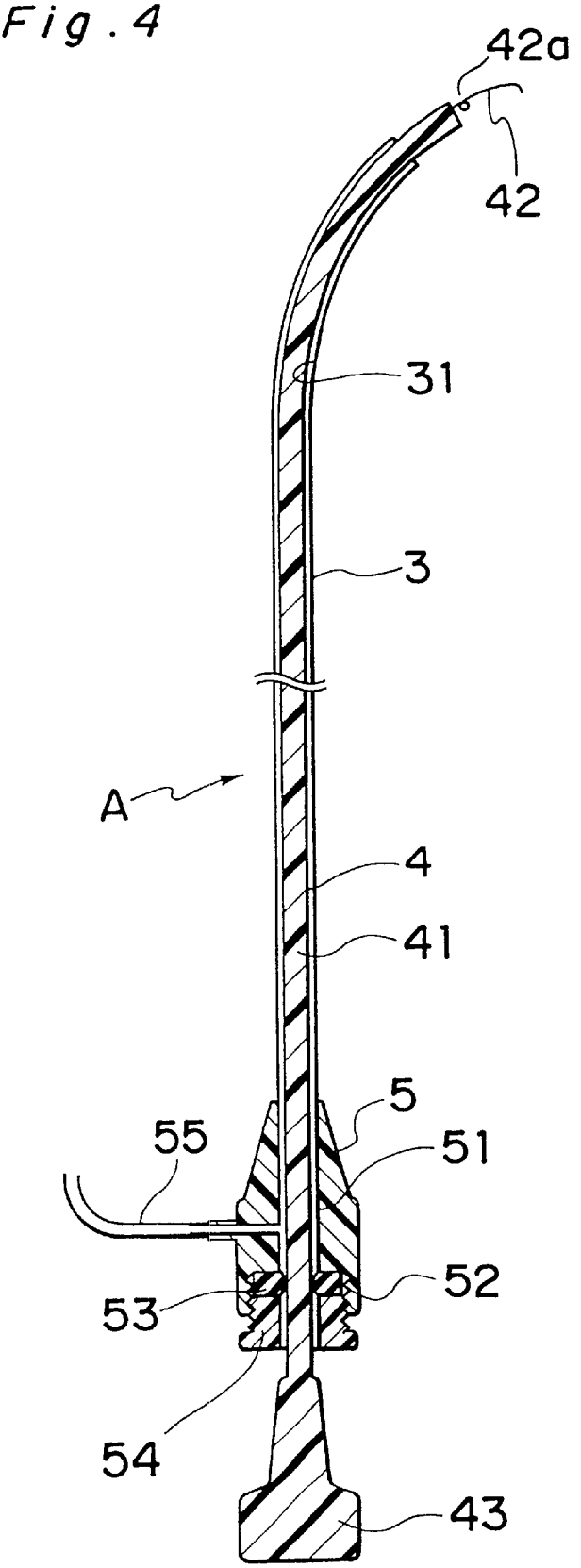
FIG. 4 is a vertical section view of a catheter assembly used for a transcatheter closure treatment in combination with the closure device of the present invention.

The second circular portion 12 may be provided at its free end with a holding portion 13 to make it possible to grasp the fixing member 1 with a catheter assembly as illustrated in FIG. 4.

Figure 2:
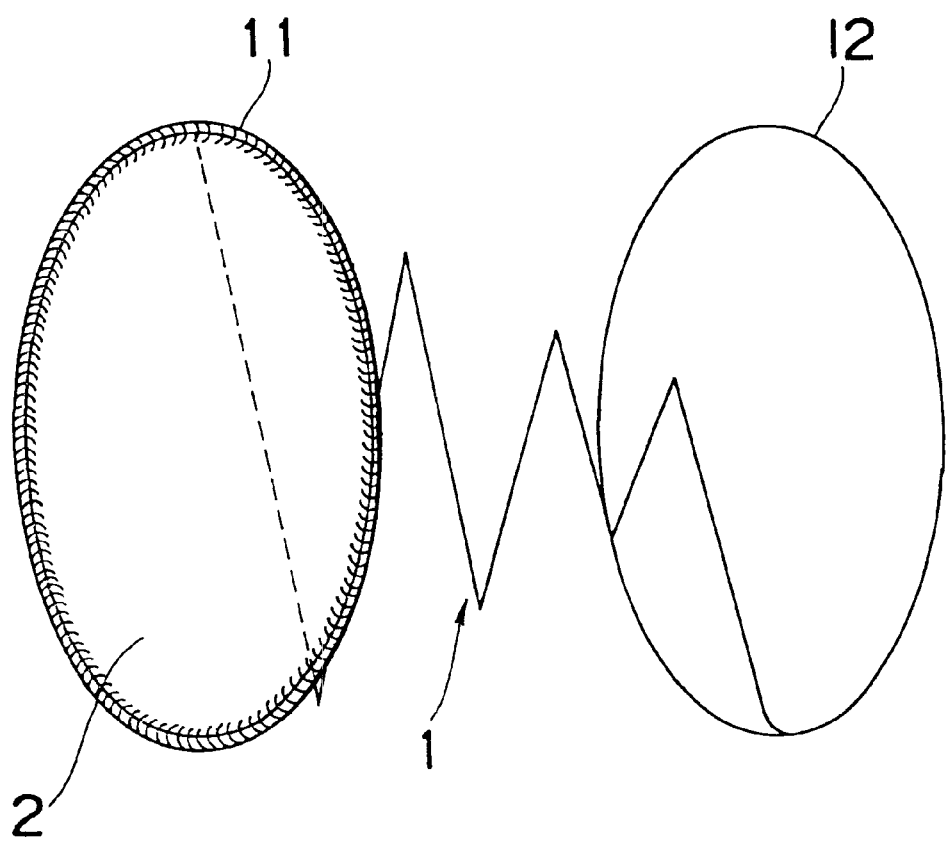
FIG. 2 is a perspective view illustrating another embodiment of a closure device for transcatheter operations according to the present invention.

The second circular portion 12 may be unfixed in a ring as shown in FIG. 1 or fixed circle in a ring as shown in FIG. 2. However, if the second circular portion 12 is not fixed in a ring, it is necessary to provide the aforesaid holding portion 13 on the free end of the second circular portion 12. On the other hand, if the second circular portion 12 is fixed in a ring, the ring of the second circular portion 12 may be closed up or covered with a closure membrane 2 as illustrated in FIG. 3.

The fixing member 1 may be formed into a spiral coil as illustrated in FIG. 1 or a zigzag as illustrated in FIG. 2 depending on the shape-restoring property or flexibility of a material used therefor. The holding portion 13 is generally formed into a small-sized ring by welding as illustrated in FIG. 1, but it may take any other configuration such as, for example, a screw-shape or a V-shape (not illustrated in the figures).

Preferably, the fixing member 1 is made of a superelastic metal wire or shape-memory-alloy wire and formed into a coil or zigzag. As a material for the fixing member, there may be used any one of superelastic metals, shape-memory-alloys having a transformation temperature ranging from 30 to 36° C. The aforesaid superelastic metal includes Ni—Ti alloys, Cu—Zn—Al alloys, Cu—Al—Ni alloys and the like. The material used for the fixing member further includes elastic metals such as stainless steels, brass and the like; and flexible resins such as polyethylene, polypropylenes, polyesters and the like.

The closure membrane 2 for closing the ring is preferably made of a woven-fabric or non-woven fabric made of a biocompatible material. The biocompatible material includes polyesters, polyethylene, polypropylene, polyamides, polyethylene fluoride, polyvinylidene fluoride, polyvinyl chloride, polyvinylidene chloride, polyurethane, cellulosic semisynthetic resins, natural fibers and the like. These materials are used in the form of a woven fabric, a non-woven fabric, a film, a porous sheet or a composite material of these materials.

The use of the closure device for transcatheter operations according to the present invention will be explained below, making reference to FIGS. 5 to 8.

At the time of transcatheter operation, the closure device C for transcatheter operations as illustrated in FIG. 1 is used in combination with a catheter assembly A, for example, as illustrated in FIG. 4.

The catheter assembly A shown in FIG. 4 comprises a sheath 3 and an elongated operating member 4 for introducing the closure device C of the present invention into the operative site through the sheath 3 and for performing an operation for closing a defective aperture D. The sheath 3 is capable of accommodating the folded closure device C and also holding the operating member 4 to be easily put in and out in its lumen 31.

The catheter assembly A comprises a sheath 3, and an elongated operating member 4 for introducing the closure device C into the operative site through the sheath 3 and for performing the operation of closing the defect aperture D.

The sheath 3 is a tubular member having a lumen 31 into which the operating linear member 4 is movably inserted to hold the inflected closure device C in the lumen 31 of the sheath 3. The sheath 3 is provided at the proximal end thereof with a connector 5 having a through-hole 51 and a large-sized threaded bore 52.

The connector 5 is provided with hemostatic means or a hemostatic valve for preventing the leakage of blood during an operation. The hemostatic means is composed of a packing 53 having a through-hole in a central part thereof and is pressed against the bottom of the threaded bore 52 by a screw bolt 54. The screw bolt 54 is provided at a central portion thereof with a through-hole serving as an inlet for the operating member 4. The connector 5 is further provided with a lateral tube 55 through which a heparinized physiological saline is infused into the sheath 3 to prevent the blood coagulation during operation.

The operating member 4 is composed of an elongated flexible member 41 and provided at a distal end thereof with a holding means 42 for releasably holding the closure device C. Preferably, the holding means 42 is a flexible linear member extending in the axial direction of the operating member 4. The proximal end of the holding means 42 is preferably winded round one time to form a circular portion 42a as shown in FIG. 4 that makes it easy to inflect the holding means 42. A handle 43 is provided for manipulating the operating member 4.

The holding means 42 can be inflected to hold the closure device C, pulled into the sheath 3 together with closure device C, and then returned to its original state extending in the axial direction of the operating member 4 to release the closure device when the closure device C is pushed out of the sheath 3.

Figure 5:
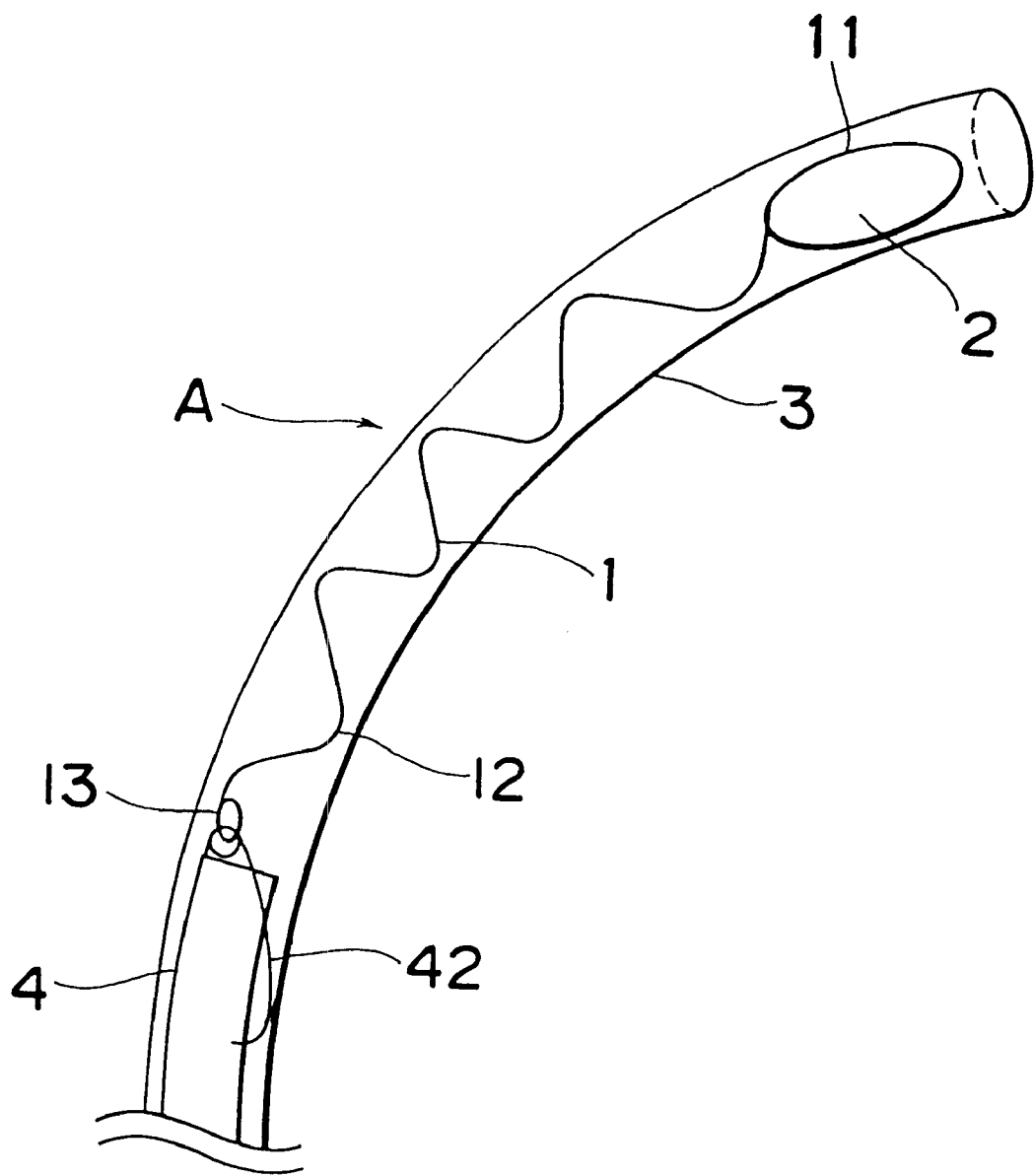
FIGS. 5–8 are illustrations of procedures in transcatheter closure treatment employing the closure device of FIG. 1 and the catheter assembly of FIG. 4.

In use, the holding means 42 of the operating member 4 of the catheter assembly A is first pushed out of the distal end of the sheath 3 as shown in FIG. 4, and then inserted into the small-sized holding portion 13 that has been provided at the free end of the second circular portion 12 of the fixing member 1 of the closure device C. Then, the holding means 42 is inflected by turning the distal end thereof toward the proximal end thereof so that the closure device C is held by the holding portion 13. Under such a condition, by pulling back the operating member 4, the closure device C is deformed into an elongated shape, pulled from the second circular portion 12 thereof into the sheath 3, and held in the sheath 3 as shown in FIG. 5.

Then, the thus prepared catheter assembly A is inserted into an elongated sheath (not illustrated in the figures) that has been previously introduced into the body of a patient through the femoral vein of the right leg to a neighborhood of a patent ductus arteriosus D of the pulmonary artery. After introducing the distal end of the catheter assembly A into an arterial canal through the pulmonary artery, the operating member 4 is pushed into the sheath 3 till the first circular portion 11 of the closure device C is pushed out of the sheath 3.

Figure 6:
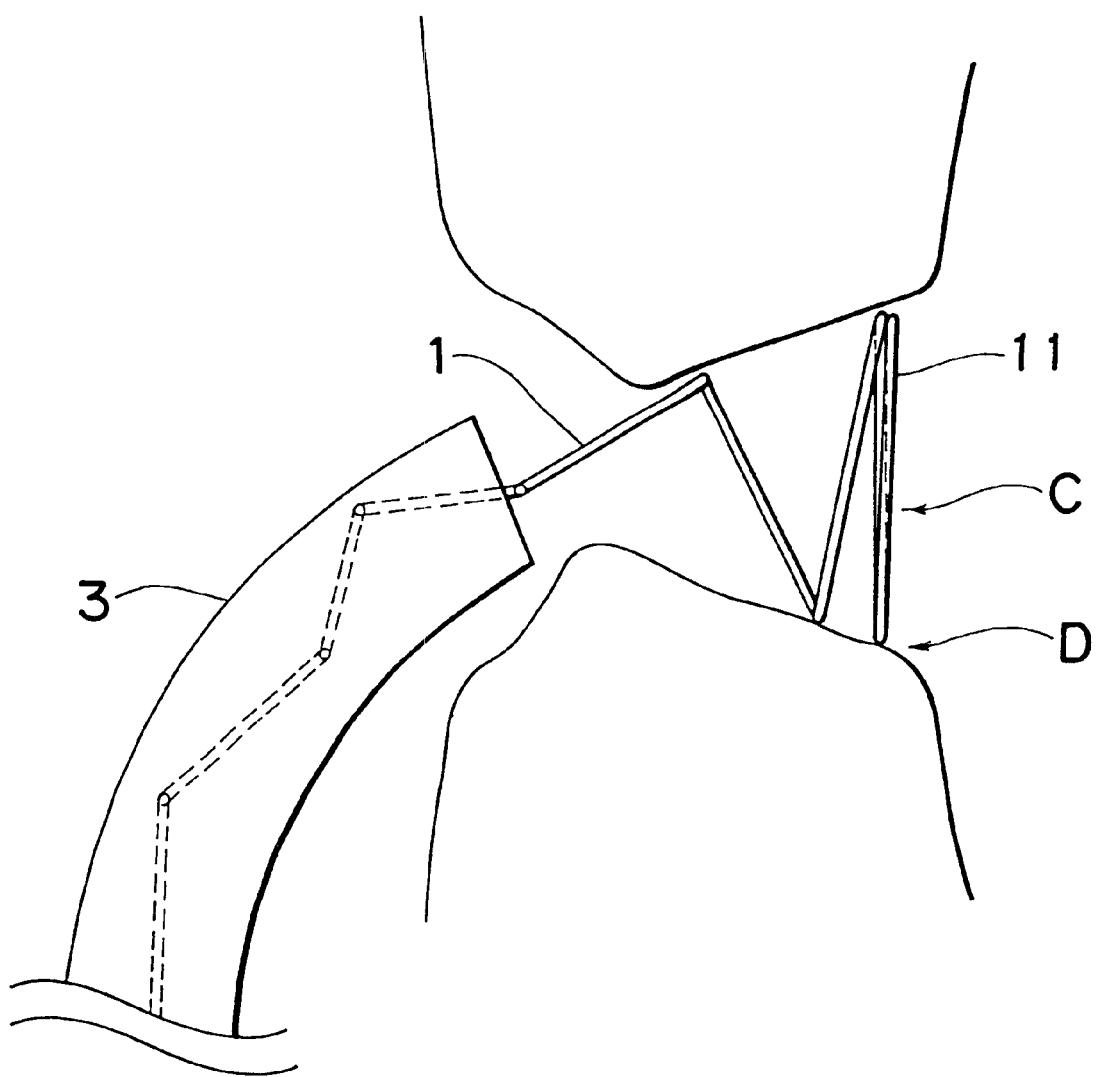
Figure 7:
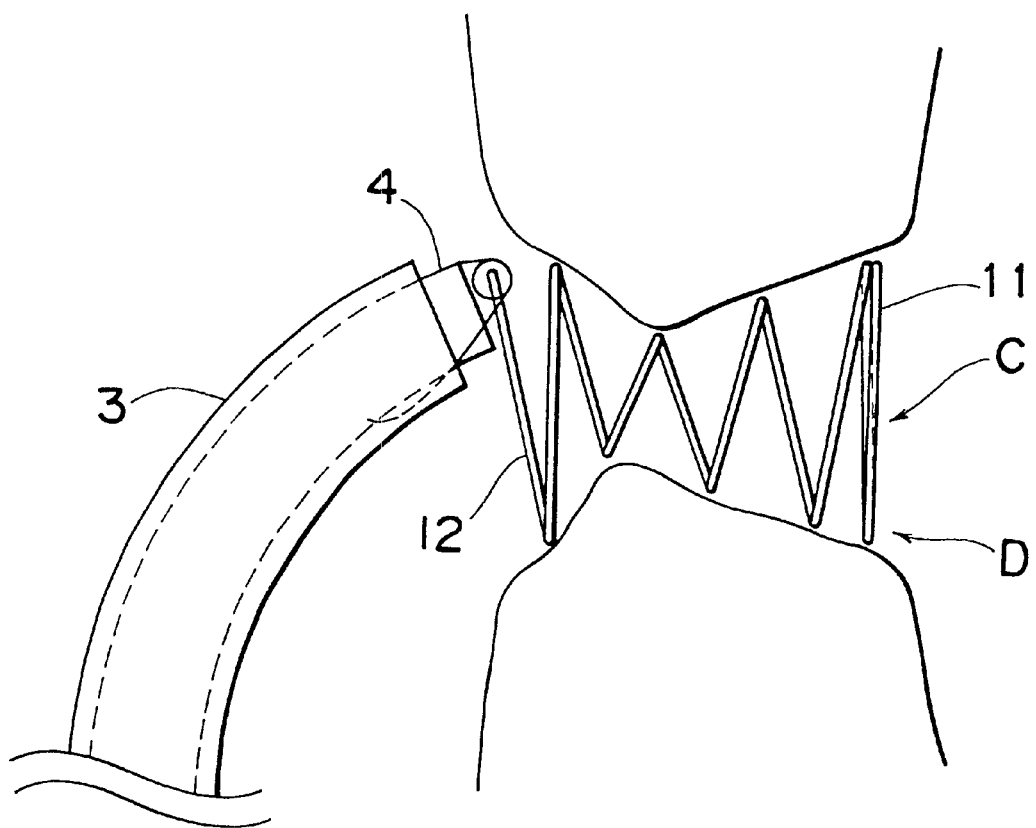

Then, the catheter assembly A is pulled back until the first circular portion 11 is engaged with the wall surrounding the patent ductus arteriosus D (FIG. 6). Subsequently, the operating member 4 is further pushed into the sheath 3 so that almost all the parts of the closure device C except for the second circular portion 12 thereof is pushed out of the sheath 3 (FIG. 7). Thereafter, the catheter assembly A is further pulled back to the pulmonary artery side, and subsequently the operating member 4 is further pushed into the sheath 3 to push the second circular portion 12 to the end of the patent ductus arteriosus D or into the pulmonary artery. Thus, the closure device C is more firmly fixed to the patent ductus arteriosus D (FIG. 7).

Figure 8:
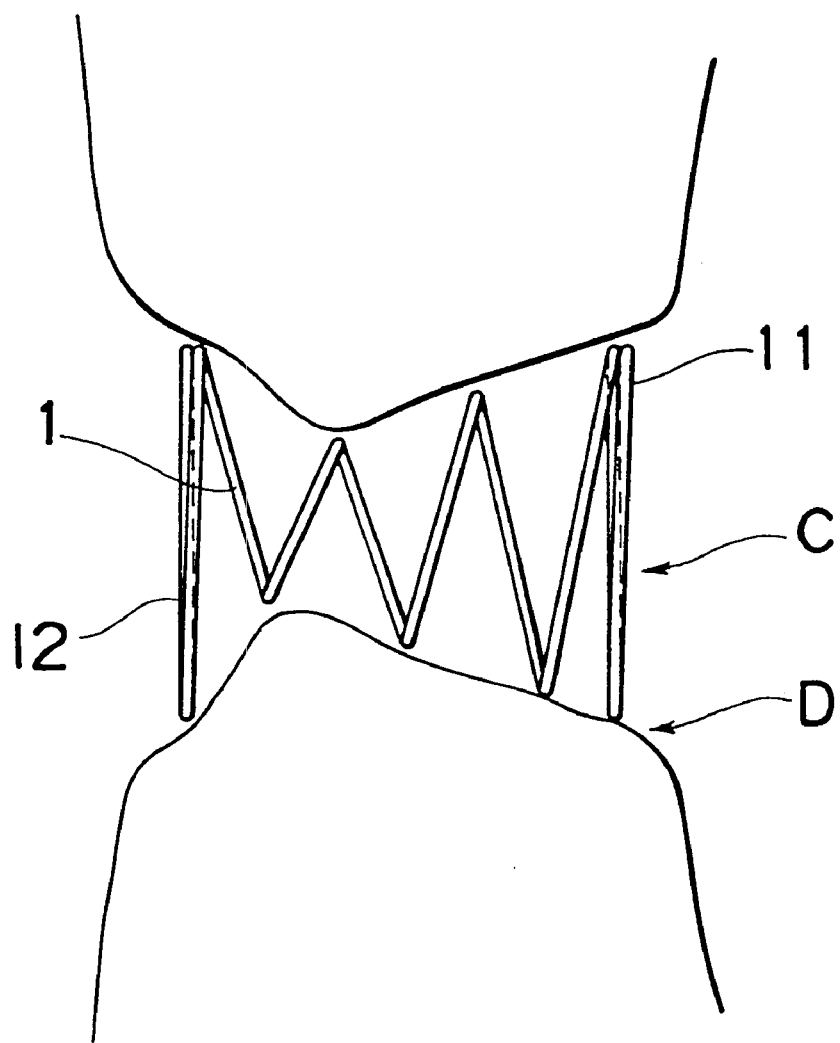

Lastly, the operating member 4 is further pushed into the sheath 3 (if necessary, by pulling back the sheath 3) to push the holding means 42 out of the sheath 3. Then, the holding means 42 returns to its original uninflected shape (i.e., the shape extending in the axial direction of the operating member 4), thereby releasing the second circular portion 12 of the closure device C from the holding means 42. At that time, the closure device C has recovered its original shape under the influence of the body temperature of the patient. Thus, the second circular portion 12 released from the holding means 42 fits on the opposite wall of the patent ductus arteriosus D so that the patent ductus arteriosus D is closed by the closure device C, thereby completing the operation. The closure device C is fixed to the tissue surrounding the patent ductus arteriosus D in the condition as illustrated in FIG. 8.

As will be understood from the above description, the closure device for transcatheter operations of the present invention makes it possible to easily and certainly close the patent ductus arteriosus. In addition, it is possible with the closure device of the present invention to solve the problems such as vessel injuries or residual shunts caused by the conventional closure devices. Further, the closure device can be retrieved with ease even in the case of dislocation or dislodgment of the closure device.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A closure device for transcatheter operations, said closure device comprising:
   a single, longitudinally elasticated fixing wire, said fixing wire having
   a shape-restoring force,
   a first end,
   a second end,
   a connecting portion, said connecting portion progressively and continually decreasing in size from the first end of said wire to the second end of said wire;
   a first circular portion secured at the first end of said wire;
   a second circular portion secured at the second end of said wire, wherein at least said first circular portion is fixedly secured in a first ring and said connecting portion secures said first circular portion to said second circular portion, and wherein the second circular portion has a free end and the second circular portion includes a second ring provided on said free end, said second ring serving as a holding portion and is relatively smaller than said first ring; and
   a closure membrane attached to said first circular portion for closing said first ring, said connecting portion being extended from the fixed circular portion and progressively decreased in size toward the opposite circular portion.

2. The closure device according to claim 9, wherein the second circular portion is fixed in a second ring.

3. The closure device according to claim 2, wherein the second ring of the second circular portion is closed up by a second closure membrane.

4. The closure device according to claim 1, wherein the closure membrane is made of a fabric or non-woven fabric of a biocompatible material.

5. The closure device according to claim 4, wherein the single fixing wire is made of a superelastic metal and is formed into a coil or zigzag shape.

6. The closure device according to claim 4, wherein the single fixing wire is made of a shape-memory alloy having a transformation temperature ranging from 30 to 36° C. and is formed into a coil or zigzag shape.

* * * * *